United States Patent
De Vries et al.

(10) Patent No.: US 9,915,596 B2
(45) Date of Patent: Mar. 13, 2018

(54) DENSITY METER FOR SLURRY

(71) Applicant: Alia Instruments Holding B.V., Enschede (NL)

(72) Inventors: Theodorus Jacobus Adrianus De Vries, Enschede (NL); Jasper Leonardus Johannes Scholten, Enschede (NL)

(73) Assignee: Alia Instruments Holding B.V., Enschede (NL)

( * ) Notice: Subject to any disclaimer, the term of this patent is extended or adjusted under 35 U.S.C. 154(b) by 158 days.

(21) Appl. No.: 15/035,243

(22) PCT Filed: Oct. 20, 2014

(86) PCT No.: PCT/NL2014/050730
§ 371 (c)(1),
(2) Date: May 9, 2016

(87) PCT Pub. No.: WO2015/069100
PCT Pub. Date: May 14, 2015

(65) Prior Publication Data
US 2016/0290908 A1    Oct. 6, 2016

(30) Foreign Application Priority Data
Nov. 7, 2013  (NL) ..................................... 2011755

(51) Int. Cl.
*G01L 9/06* (2006.01)
*G01N 9/06* (2006.01)

(52) U.S. Cl.
CPC ..................................... *G01N 9/06* (2013.01)

(58) Field of Classification Search
CPC ........................................................ G01N 9/06
See application file for complete search history.

(56) References Cited

U.S. PATENT DOCUMENTS

| | | | | |
|---|---|---|---|---|
| 1,905,558 A * | 4/1933 | Foote | ......................... | G01F 1/74 |
| | | | | 177/16 |
| 2,432,039 A * | 12/1947 | Plank | ....................... | G01N 9/06 |
| | | | | 73/434 |
| 2,669,118 A * | 2/1954 | Nichols | ..................... | G01N 9/06 |
| | | | | 73/434 |
| 3,049,919 A * | 8/1962 | Roth | ......................... | G01F 1/86 |
| | | | | 177/14 |
| 3,143,887 A | 8/1964 | Hathorn et al. | | |

(Continued)

FOREIGN PATENT DOCUMENTS

EP    0722084 A1    7/1996

*Primary Examiner* — David Bolduc
(74) *Attorney, Agent, or Firm* — The Webb Law Firm

(57) ABSTRACT

A density meter for slurry which is transported through a pipe, the density meter including: a pipe part; flexible pipe couplings arranged on either end of the pipe part; a force sensor for measuring a force in the direction of the at least one degree of freedom between the pipe part and a fixed point; an accelerometer arranged on the pipe part for measuring the accelerations of the pipe part in the direction of the at least one degree of freedom; and computing means for computing the density of the slurry in the pipe part on the basis of the volume of the pipe part, the force measured by the force sensor and the acceleration measured by the accelerometer.

11 Claims, 2 Drawing Sheets

(56) References Cited

U.S. PATENT DOCUMENTS

| | | | | |
|---|---|---|---|---|
| 3,320,791 A | * | 5/1967 | Banks | G01N 9/002 |
| | | | | 73/1.01 |
| 3,449,941 A | * | 6/1969 | Banks | G01N 9/002 |
| | | | | 73/32 A |
| 3,503,267 A | * | 3/1970 | Shiba | G01G 7/02 |
| | | | | 73/32 A |
| 3,541,863 A | * | 11/1970 | Sheldon | G01N 9/06 |
| | | | | 177/164 |
| 4,285,239 A | | 8/1981 | Heine et al. | |
| 4,476,722 A | * | 10/1984 | Bentkowski | G01N 9/06 |
| | | | | 73/434 |
| 4,611,955 A | * | 9/1986 | Doerr | B01D 21/2477 |
| | | | | 406/115 |
| 6,581,451 B2 | * | 6/2003 | Ence | G01N 9/04 |
| | | | | 73/149 |
| 7,290,447 B1 | | 11/2007 | Burnette et al. | |
| 2008/0245147 A1 | * | 10/2008 | Snieder | G01N 9/002 |
| | | | | 73/32 A |
| 2013/0145843 A1 | * | 6/2013 | Cordeiro | E21B 47/0005 |
| | | | | 73/32 A |

* cited by examiner

DENSITY METER FOR SLURRY

CROSS-REFERENCE TO RELATED APPLICATIONS

This application is the United States national phase of International Application No. PCT/NL2014/050730 filed Oct. 20, 2014, and claims priority to The Netherlands Patent Application No. 2011755 filed Nov. 7, 2013, the disclosures of which are hereby incorporated in their entirety by reference.

BACKGROUND OF THE INVENTION

Field of the Invention

The invention relates to a density meter for slurry which is transported through a pipe.

Description of Related Art

Such measurements are made for instance on a dredging vessel in order to enable monitoring of the dredging process and to make optimum use of the equipment. During dredging gravel, sand and/or soil are dislodged from the bottom of for instance a waterway and pumped upward with a certain amount of water into the vessel. If the density of this pumped-up slurry is too low, the vessel will be filled mainly with water instead of with gravel, sand and soil.

Gravel, sand and/or soil are also transported in a slurry in the same way in for instance the mining industry, where it is likewise desirable for the purpose of monitoring the process to be able to make a density measurement of the slurry.

Known in the prior art are density meters for slurry which make use of radioactive radiation. The radioactive radiation here passes through the pipe with the slurry and the transmitted radiation is received at a sensor with which an indication of the density of the slurry can be obtained.

The drawback of such a density meter is that because of the use of radioactive radiation strict requirements are set in respect of operative personnel and for handling of the density meter. In addition, legislation requires that personnel have to be highly trained and that the transport of such a density meter has to comply with strict requirements. Such a density meter is moreover slow in determining the density of the slurry, thereby resulting in slow control of the dredging process.

EP07220841 describes a density meter wherein a pipe part is suspended freely between a feed pipe and a discharge pipe. Arranged over this pipe part is a portal which rests on the feed pipe and the discharge pipe. Further provided between this portal and the pipe part is a weighing cell which measures the weight of the pipe part.

In a static application the weight of the slurry in the pipe part can be measured with such a density meter and, combined with the volume of the pipe part, the density can be calculated.

As soon as this density meter is used on a vessel which rolls and pitches because of waves, the weight measurement of the pipe part will no longer be representative. Owing to for instance an up and downward movement of the pipe part the measured weight will come out higher or lower than the actual weight.

According to this publication such variations in the measured weight can be filtered out, but this will make the determination of the density of the slurry slower because measurements have to be taken over a longer period, whereby the dredging process can be controlled less quickly.

It is an object of the invention to reduce or even obviate the above stated drawbacks of the prior art.

SUMMARY OF THE INVENTION

This object is achieved according to the invention with a density meter, comprising:
a pipe part;
flexible pipe couplings arranged on either end of the pipe part for coupling the pipe part to a feed pipe and a discharge pipe, which pipe couplings impart to the pipe part at least one degree of freedom relative to the feed pipe and the discharge pipe;
a force sensor for measuring a force in the direction of the at least one degree of freedom between the pipe part and a fixed point, such as a floor;
an accelerometer arranged on the pipe part for measuring the accelerations of the pipe part in the direction of the at least one degree of freedom; and
computing means for computing the density of the slurry in the pipe part on the basis of the volume of the pipe part, the force measured by the force sensor and the acceleration measured by the accelerometer.

With the density meter according to the invention the pipe part through which the slurry flows has at least one degree of freedom. The at least one degree of freedom preferably lies in the direction of the gravitational force. The force sensor measures the force exerted between the pipe part and the fixed point, such as for instance a ground surface.

In addition, the absolute acceleration of the pipe part in the direction of the degree of freedom is also measured. In a stationary state, wherein the degree of freedom is the same as the gravitational force direction, the absolute acceleration of the pipe part will be equal to the gravitational acceleration g.

On the basis of the measured acceleration and the measured force the mass of the pipe part, including the slurry, can then be calculated. Combined with the volume of the pipe part and the mass of the pipe part, the density of the slurry can subsequently be determined.

If the ground surface and thereby the pipe part now move, for instance because the pipe part is arranged on a moving vessel, the measured acceleration will vary from the gravitational acceleration g, but the measured force will also vary in the same proportion, whereby the resulting mass will be equal to the mass which would be calculated in a static arrangement.

Using the density meter according to the invention the density can moreover be measured at an angle of the degree of freedom changing relative to the direction of gravitational force.

The mass of the slurry, and thereby the density, can be measured with the density meter according to the invention irrespective of movements of the ground surface and the pipe part. A rapid determination of the density of the slurry in the pipe part is hereby possible, which can be used for instance for information to the operator or for the purpose of controlling for instance a dredging process.

The accelerometer can be arranged directly onto the pipe part, although it is also possible to arrange the accelerometer on the pipe part via a body coupled therebetween.

A preferred embodiment of the density meter according to the invention further comprises a support for supporting the pipe part on a ground surface, wherein the force sensor is arranged between the support and the pipe part.

By arranging a support a rigid suspension of the pipe part and the force sensor can be obtained, whereby the force measurement is not disrupted by possible fluctuations between the ground surface and the pipe part. In addition, the support ensures that the pipe part is arranged axially with a feed and discharge pipe, whereby the flexible pipe couplings can impart sufficient freedom to the pipe part to enable a good measurement.

In another embodiment of the density meter according to the invention the support comprises a linear guide for guiding the pipe part in the measuring direction of the force sensor.

In order to prevent the force measured by the force sensor being affected by transverse forces, a linear guide is provided in this embodiment which guides the pipe part in the measuring direction and thereby limits the pipe part in the other direction. Possible disruptions by transverse forces during the measurement in the direction of the at least one degree of freedom are thus prevented.

In another embodiment of the density meter according to the invention the support supports on at least one of the feed pipe and the discharge pipe.

In another preferred embodiment of the density meter according to the invention the pipe couplings comprise a flexible connecting sleeve. The flexible connecting sleeves provide a limp connection between the feed pipe and discharge pipe so that the pipe part can move as freely as possible and the measurements of the force sensor are affected minimally.

The invention further relates to a combination of a density meter according to the invention, a feed pipe, a discharge pipe and a ground surface, wherein the pipe part of the density meter is arranged with one pipe coupling on the feed pipe and is arranged with the other pipe coupling on the discharge pipe, and wherein the force sensor is arranged between the pipe part and the ground surface.

BRIEF DESCRIPTION OF THE DRAWINGS

These and other features of the invention are further elucidated with reference to the accompanying drawings.

DESCRIPTION OF THE INVENTION

Figure 1:
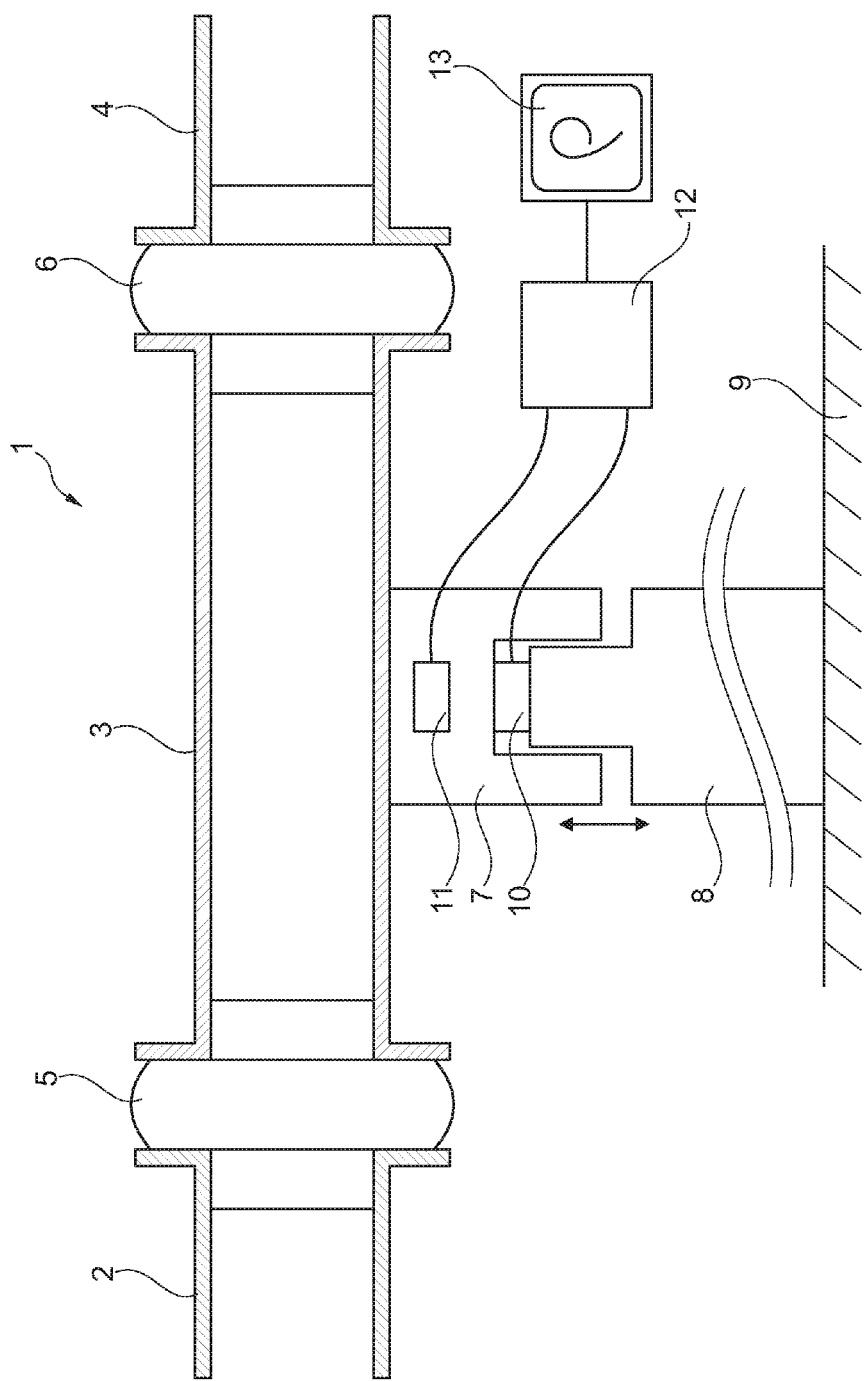
FIG. 1 shows a schematic representation of a first embodiment of a combination according to the invention.

A first embodiment of a combination 1 according to the invention is shown in FIG. 1. Combination 1 has a feed pipe 2, a pipe part 3 and a discharge pipe 4. Pipe part 3 is connected on either side via flexible rubber sleeves 5, 6 to feed pipe 2 and discharge pipe 4. The flexible sleeves 5, 6 ensure that slurry from feed pipe 2 can flow via pipe part 3 to discharge pipe 4 while pipe part 3 can move freely in radial direction.

Pipe part 3 is supported by a two-part support 7, 8 on a ground surface 9, such as for instance a concrete floor or ground. Supports 7, 8 slide telescopically into each other, whereby the movement of pipe part 3 is limited to a single degree of freedom, and this in vertical direction.

Arranged between first support part 7 and second support part 8 is a force sensor 10 which measures the force exerted between pipe part 3 and ground surface 9.

Further provided on first support part 7 is an accelerometer 11 which measures the absolute accelerations of pipe part 3 in the direction of the degree of freedom.

Using the formula F=ma computer unit 12 can easily compute the mass of pipe part 3 including the slurry flowing therethrough. Using the internal volume of pipe part 3 and the net mass of pipe part 3 it is then possible to compute the density ρ of the slurry flowing through pipe part 3. This density ρ can for instance be displayed on a screen 13 and/or be used in a further control, for instance of a dredging process or a mining industry process. Depending on the flexibility of sleeves 5, 6, it may be that at least a part of the internal volume of sleeves 5, 6 has to be taken into account in the calculation, since this part can affect the force measurement.

Figure 2:
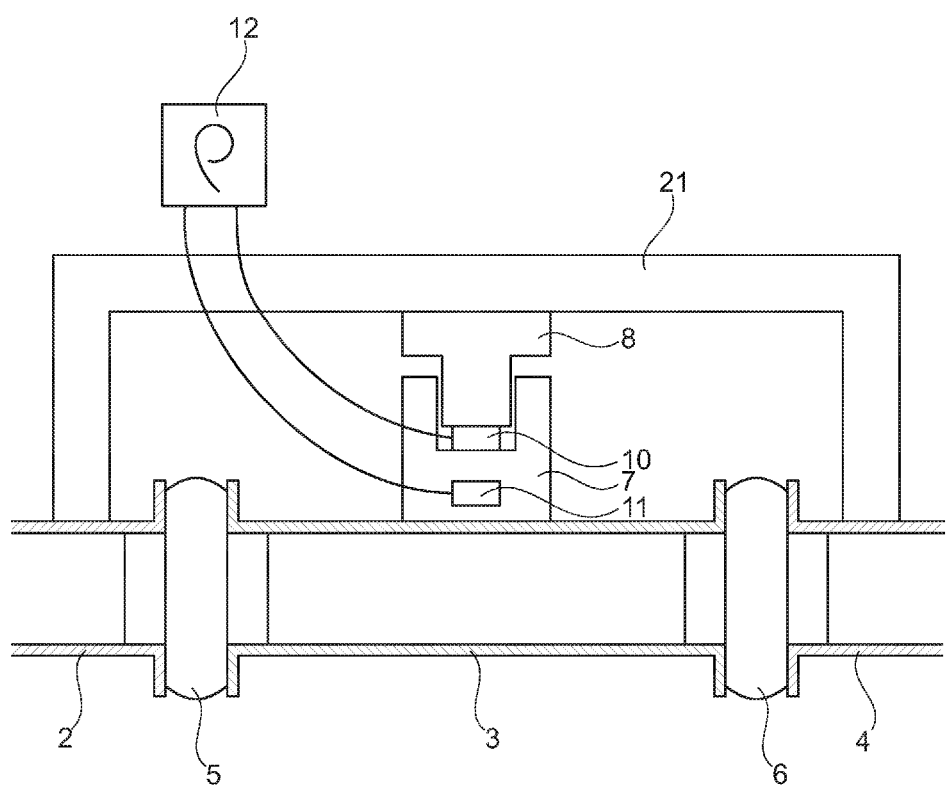
FIG. 2 shows a schematic representation of a second embodiment of a combination according to the invention.

Shown in FIG. 2 is a second embodiment 20 of a combination according to the invention which partially corresponds to the embodiment 1 according to FIG. 1. The same components are therefore designated with the same reference numerals.

In this embodiment 20 the pipe part 3 is suspended from a portal 21 which supports on feed pipe 2 and discharge pipe 4. First support part 7 and second support part 8 here ensure that the degree of freedom is once again limited to the vertical direction, and moreover that pipe part 3 is suspended in neutral position coaxially with feed pipe 2 and discharge pipe 4.

In this embodiment 20 the force sensor 10 will also measure the force exerted between portal 21 and pipe part 3, and accelerometer 11 will measure the acceleration in vertical direction, whereby computer unit 12 can compute the density ρ of the slurry.

The invention claimed is:

1. A density meter for slurry which is transported through a pipe, the density meter comprising:
   a pipe part;
   flexible pipe couplings arranged on either end of the pipe part for coupling the pipe part to a feed pipe and a discharge pipe, which pipe couplings impart to the pipe part at least one degree of freedom relative to the feed pipe and the discharge pipe;
   a force sensor for measuring a force in a direction of the at least one degree of freedom between the pipe part and a fixed point;
   an accelerometer arranged on the pipe part for measuring the accelerations of the pipe part in the direction of the at least one degree of freedom; and
   computing means for computing a density of the slurry in the pipe part on the basis of a volume of the pipe part, the force measured by the force sensor and the acceleration measured by the accelerometer.

2. The density meter as claimed in claim 1, further comprising a support for supporting the pipe part on a ground surface, wherein the force sensor is arranged between the support and the pipe part.

3. The density meter as claimed in claim 2, wherein the support comprises a linear guide for guiding the pipe part in the measuring direction of the force sensor.

4. The density meter as claimed in claim 2, wherein the support supports on at least one of the feed pipe and the discharge pipe.

5. The density meter as claimed in claim 1, wherein the pipe couplings comprise a flexible connecting sleeve.

6. A combination comprising a density meter as claim 1, a feed pipe, a discharge pipe and a ground surface, wherein the pipe part of the density meter is arranged with one pipe coupling on the feed pipe and is arranged with the other pipe coupling on the discharge pipe, and wherein the force sensor is arranged between the pipe part and the ground surface.

7. The density meter as claimed in claim 1, wherein the fixed point is a floor.

8. The density meter as claimed in claim 3, wherein the support supports on at least one of the feed pipe and the discharge pipe.

9. The density meter as claimed in claim 2, wherein the pipe couplings comprise a flexible connecting sleeve.

10. The density meter as claimed in claim 3, wherein the pipe couplings comprise a flexible connecting sleeve.

11. The density meter as claimed in claim 4, wherein the pipe couplings comprise a flexible connecting sleeve.

* * * * *